(12) United States Patent
Jin et al.

(10) Patent No.: US 7,102,020 B2
(45) Date of Patent: Sep. 5, 2006

(54) TOTAL SYNTHESIS OF DAURICHROMENIC ACID

(76) Inventors: Zhendong Jin, 209 Holiday Rd., #335, Coralville, IA (US) 52241; Ying Kang, 560 Hawkeye Ct., Iowa City, IA (US) 52246

(*) Notice: Subject to any disclaimer, the term of this patent is extended or adjusted under 35 U.S.C. 154(b) by 8 days.

(21) Appl. No.: 10/739,882

(22) Filed: Dec. 18, 2003

(65) Prior Publication Data

US 2004/0192762 A1 Sep. 30, 2004

Related U.S. Application Data

(60) Provisional application No. 60/435,417, filed on Dec. 20, 2002.

(51) Int. Cl.
*C07D 311/74* (2006.01)
*C07D 311/76* (2006.01)

(52) U.S. Cl. ........................... 549/399; 549/406

(58) Field of Classification Search ............... 549/399, 549/400; 514/454, 456; 8/579; 504/292; 204/157, 69
See application file for complete search history.

(56) References Cited

OTHER PUBLICATIONS

Kashiwada, Y., et al., "Isolation of Rhododaurichromanic Acid B And The Anti-HIV Principles Rhododaurichromanic Acid A And Rhododaurichromenic Acid From Rhododendron Dauricum", *Tetrahedron*, 57, (2001),1559-1563.

*Primary Examiner*—Cecilia J. Tsang
*Assistant Examiner*—Raymond Covington
(74) *Attorney, Agent, or Firm*—Schwegman, Lundberg, Woessner & Kluth, P.A.

(57) ABSTRACT

The present invention provides a method to prepare 2H-benzo[6]pyrans, such as the anti-HIV natural product daurichromenic acid (1a), by microwave-assisted tandem aldol reaction of a phenolic enolate followed by intramolecular SN2' type cyclization to form the 2H-benzo[6]pyran core structure.

13 Claims, 2 Drawing Sheets

TOTAL SYNTHESIS OF DAURICHROMENIC ACID

CROSS-REFERENCE TO RELATED APPLICATIONS

This application claims priority to U.S. provisional application Ser. No. 60/435,417, filed Dec. 20, 2002.

BACKGROUND OF THE INVENTION

Daurichromenic acid (1a) was isolated from the leaves and twigs of *Rhododendron dauricum*, a plant that is distributed in the northern part of China, eastern part of Siberia, and Hokkaido. See, e.g., Kashiwada, Y. et al., *Tetrahedron*, 57, 1559 (2001); Jpn. Kokai Tokko Koho, JP 82-28, 080, 1982. It belongs to the family of chromene natural products. Two novel chromane derivatives rhododaurichromanic acids A (5a) and B (6b) were also isolated from the same plant:

1a

5a

6a

Synthesis of 2H-benzopyrans (chrom-3-enes) has been the subject of many investigations. Dotz, K. H. *Pure & Appl. Chem.* 1983, 55, 1689 and references cited therein; (b) Henry, G. E.; Jacobs, H. *Tetrahedron* 2001, 57, 5335; (c) Chang, S. et al., *J Org. Chem.* 1998, 63, 864; (d) Saimoto, H. et al., *J Org. Chem.* 1996, 61, 6768; (e) North, J. T. et al., *J Org. Chem.* 1995, 60, 3397; (f) Gabbutt, C. D. et al., *Tetrahedron* 1994, 50, 2507; (g) Cruz-Almanza, R. et al., *Heterocycles* 1994, 37, 759; (h) Rao, U. et al., *Tetrahedron Lett.* 1983, 24, 5023; (i) Sartori, G. et al., *J. Org. Chem.* 1979, 44, 803. The reaction developed by Shigemasa appeared to be quite promising for the synthesis of this class of natural products. Saimoto, H. et al., *J Org. Chem.*, 1996 61, 6768. Unfortunately, the reaction between 16 and 3a is extremely slow under Shigemasa's conditions (see FIG. 1). The mixture gave only 15% yield of the desired product 4a (B=Et) after heating at reflux for four days (see Table 1, hereinbelow, entry 1). The yield was improved to 32% when the mixture was heated at 90° C. in a sealed tube for one day (Table 1, entry 2). However, the reaction stopped, and the yield is not improved even with the addition of excess of aldehyde 3a and with longer heating time.

Therefore, a need exists for effective methods to prepare daurichromenic acid and analogs thereof.

SUMMARY OF THE INVENTION

The present invention provides an efficient synthesis of benzo[b]pyrene (chromo-3-ones), including the potent anti-HIV natural product, daurichromenic acid (1a), as well as related compounds, including intermediates useful for the synthesis thereof. The synthesis involves a microwave-assisted tandem aldol reaction of a phenolic enolate, followed by intramolecular SN2' type cyclization to form the 2H-benzo-pyran core structure. In one embodiment, the present invention provides a method for preparing daurichromenic acid (1a), comprising (a) reacting 2-methyl-4,6-dihydroxybenzoic acid having a carboxy-protecting group with a compound of the formula (3a):

(3a)

in the presence of an effective amount of $CaCl_2$—$2H_2O$, $NEt_3$ and microwave irradiation to yield a compound of the formula (4a):

(4a)

wherein B is a carboxy-protecting group, and (b) removing B to yield daurichromenic acid. Useful carboxy-protecting groups (B), include 2-Me$_3$Si-(ethyl), (C$_1$–C$_4$) alkyl, (C$_1$–C$_4$)$_3$ Si, benzyl and the like.

Reversible protection of functional groups such as amino, carboxyl, hydroxyl, and thiol is disclosed in *Compendium of Organic Synthetic Methods*, I. T. Harrison et al., eds., Wiley-Intersciences, New York, N.Y. (1971), and in U.S. Pat. No. 5,457,208. Examples of organic groups useful as substitutents are R$^{18}$ or R$^{19}$ as disclosed in U.S. Pat. No. 5,877,180, at cols. 8–9. See, also, e.g., Green and Wuts, *Protecting Groups in Organic Synthesis*, John Wiley (3d ed. 1999). Daurichromenic acid can be further converted by irradiation to bioactive compounds such as rhododurichromenic acid A (5a) and rhododurichromenic acid (6a).

More generally, the present invention also provides a method for preparing a compound of formula (1)

(1)

wherein R, X, Y, and Z are organic substituents that do not interfere with the condensation of (2) and (3), such as those that comprise functional groups that are protected by removable protecting groups, comprising (a) condensing a compound of formula (2):

(2)

wherein R' is a carboxylic acid protecting group, with a compound of formula (3):

(3)

in the presence of an effective amount of CaCl$_2$, N[(C$_2$–C$_4$) alkyl]$_3$ and [(C$_1$–C$_4$)alkyl]OH and microwave irradiation to yield a compound of formula (4):

(4)

and (b) optionally removing protecting R' to yield a compound of formula (1).

Useful X, Y and Z include (C$_1$–C$_2$)alkyl, preferably (C$_1$–C$_4$)alkyl, (C$_8$–C$_{10}$)aryl, alkylaryl, aralkyl, alkaralkyl, wherein the alkyl groups optionally comprise 1–3 double bonds, and can be interrupted by 1–2O or N(C$_1$–C$_4$)alkyl and/or substituted by functional groups that do not interfere with the condensation reaction. R can have the same definition and is preferably a terpenoid group as will be further discussed below.

Preferably, Y is (C$_1$–C$_4$)alkyl, such as methyl; X and/or Z are H; N[(C$_2$–C$_4$)alkyl]$_3$ is NEt$_3$ (triethylamine) and [(C$_1$–C$_4$)alkyl]OH is EtOH (ethanol).

Preferably R' is 2-(trimethylsilyl)ethyl or triethylsilylethyl. However, R' can be any carboxy-protecting group that will survive the condensation conditions and can be removed under conditions that do not degrade compound 4. For example, when R' is 2-(trimethylsilyl)ethyl, it can be removed from TBAF (tributyl ammonium fluoride).

Preferably, R is C$_3$–C$_{22}$ alkyl optionally comprising 1–3 double bonds. In a preferred embodiment, R is a terpene, e.g., a terpene connected to the ring by a single covalent bond.

Terpenes useful in the present invention are known and available to the art. For example, see F. C. Whitmore, *Organic Chemistry*, Vol. 1, Dover Pub., NY (1951) at pp. 553–561; A. Streitweiser et al., *Introduction to Organic Chemistry*, MacMillan Pub., NY (1976), at 643–645; 1158–1164. Aldehydes such as 3 can be readily prepared by the MnO$_2$ oxidation of terpenols.

When X is H, the present method further comprises irradiating the compound of formula 1, wherein R is —CH$_2$CH$_2$CH=C(CH$_3$)R$^2$, wherein R$^2$ is the remainder of organic group R, to yield a compound of formula (6):

(6)

Preferably, R$^2$ is —CH$_2$CH$_2$CH=C(Me)$_2$; Y is CH$_3$ and Z is H.

Another embodiment of the invention provides a method for preparing daurichromenic acid (1a), comprising (a) reacting 2-methyl-4,6-dihydroxybenzoic acid having a carboxy-protecting group (B) with a compound of the formula (3a):

(3a)

in the presence of an effective amount of CaCl$_2$—2H$_2$O, NEt$_3$ and microwave irradiation to yield a compound of the formula (4a):

(4a)

wherein B is a carboxy-protecting group, such as 2-TMS (ethyl) or (C$_1$–C$_4$)alkyl and (b) removing B to yield daurichromenic acid.

As noted above, compound (1a) can be converted into rhododaurichromenic acid A (5a) and rhododaurichromenic acid B (6a) by irradiation.

The present invention also provides a therapeutic or diagnostic method comprising use of a compound of formula 1, 4, 6, 1a, 4a, 5a, or 6a to inhibit HIV growth in vitro or in vivo. The compounds can be used singly or in combination to treat a viral infection such as HIV infection or to treat AIDS in a mammal, such as a human, in need of such treatment, comprising administering an effective amount of said compound to said mammal, such as a human patient.

Thus, the present invention also provides a composition, such as a pharmaceutical composition, comprising an effective amount of a compound of formula 1, 4, 6, 1a, 4a, 5a, or 6a in combination with a carrier or vehicle, such as a pharmaceutically acceptable liquid or solid carrier or vehicle.

Doses and dosage forms useful to treat mammals infected with HIV or other viral infections are disclosed in U.S. Pat. No. 5,567,703. Dosages for humans and other mammals can be extrapolated from dosages effective in mice by the methods disclosed in U.S. Pat. No. 5,294,430.

Compounds of formulae 1a, 1, 4, 6, 4a, 5a or 6a can also be used as antibacterials or herbicides, or can be used as dyestuffs.

BRIEF DESCRIPTION OF THE FIGURES

FIG. 2 depicts a synthetic route to daurichromenic acid (1a) and to 5a and 6a.

DETAILED DESCRIPTION OF THE INVENTION

Figure 1:
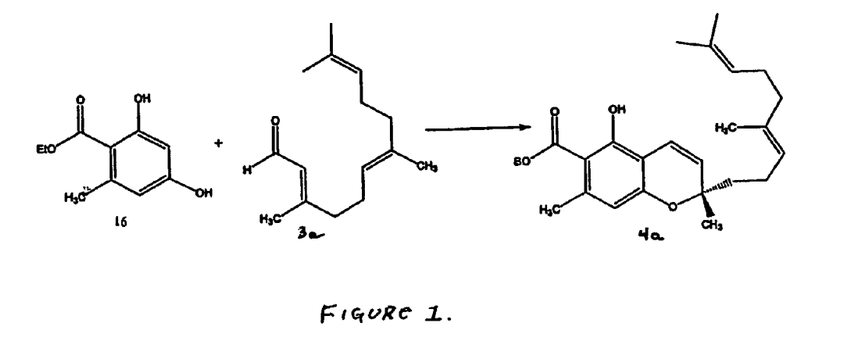
FIG. 1 summarizes a synthetic route to protected daurichromenic acid (4a).

Because the intramolecular SN2' type cyclization is a fast reaction, the overall slow reaction is presumably due to the high activation energy in the aldol reaction of the phenolic enolate (FIG. 1). It is known that microwave irradiation can accelerate many reactions. See, e.g., Chadick, S., *Tetrahedron*, 1995, 51; Galema, S.A., *Chem. Soc. Rev.*, 1997, 26, 233. A much faster reaction was indeed observed when the reaction mixture was placed in a sealed 60 mL Teflon pressure vessel (Savillex Corp.) filled with argon, and irradiated in a microwave oven (Panasonic Model NN5740 (1200 W)). After only 3 minutes of irradiation, compound 4a (B=Et) was isolated in 23% yield (entry 3). However, the yield did not improve with longer irradiation time or with the addition of more aldehyde 3a. After screening a few different reaction conditions, it was found that the reaction between 6 and 3a in the presence of CaCl$_2$•2H$_2$0, NEt$_3$, and EtOH provided 50% yield of the desired product 4a, and it took only 20 minutes of microwave irradiation (Table 1, entry 4). When no microwave irradiation was used, the yield of compound 4a was only 5% (Table 1, entry 5).

In entry 6, the mixture of compound 3a (2.0 eq.) and compound 6 (1.0 eq.) were irradiated for 20 minutes. Then another 1.0 eq. of compound 3a was added and the mixture was irradiated again for 20 minutes. Using these conditions, compound 4a was isolated in 70% yield. It should be noted that in the absence of CaCl$_2$•2H$_2$O, NEt$_3$, and EtOH, only trace amount of compound 4a was isolated when the reaction was run in pyridine (Table 1, entry 7). See, Subburaj, K., et al., *Bull. Chem. Soc. Jpn.*, 1999, 72, 259.

Table 1. Various Conditions for the Formation of 2H-bezopyran, the Core Structure of Daurichromenic Acid (4a, B=Et)

| Entry | Conditions | Yield |
|---|---|---|
| 1 | 5 (1.2 eq.), Ca(OH)$_2$ (0.83 eq.), MeOH, reflux, 4 d | 15% |
| 2 | 5 (1.2 eq.), Ca(OH)$_2$ (0.83 eq.), MeOH, sealed tube, 90° C., 1d | 32% |
| 3 | 5 (1.2 eq.), Ca(OH)$_2$ (0.83 eq.), MeOH, microwave irradiation, 1 min × 3 | 23% |
| 4 | 5 (1.2 eq.), CaCl$_2$.2H$_2$O, (0.83 eq.), NEt$_3$ (3.32 eq.), EtOH, microwave irradiation, 1 min × 20 | 50% |
| 5 | 5 (1.2 eq.), CaCl$_2$.2H$_2$O (0.83 eq.), NEt$_2$ (3.32 eq.), EtOH, reflux, 2d | <5% |
| 6 | i) 5 (2.0 eq.), CaCl$_2$.2H$_2$O (0.83 eq.), NEt$_3$ (3.32 eq.), EtOH, microwave irradiation, 1 min × 20; ii) 5 (1.0 eq.), microwave irradiation, 1 min × 20 | 70% |
| 7 | 5 (2.0 eq.), Pyridine, microwave irradiation, 25 min | <5% |

The hydrolysis of the ethyl ester functionality of compound 4a (B=Et) to daurichromenic acid (1) proved to be difficult. The best conditions for ester hydrolysis (3M NaOH in MeOH/H$_2$O at 40° C. for 3 days) provided daurichromenic acid (1a) in 40% yield.

Figure 2:
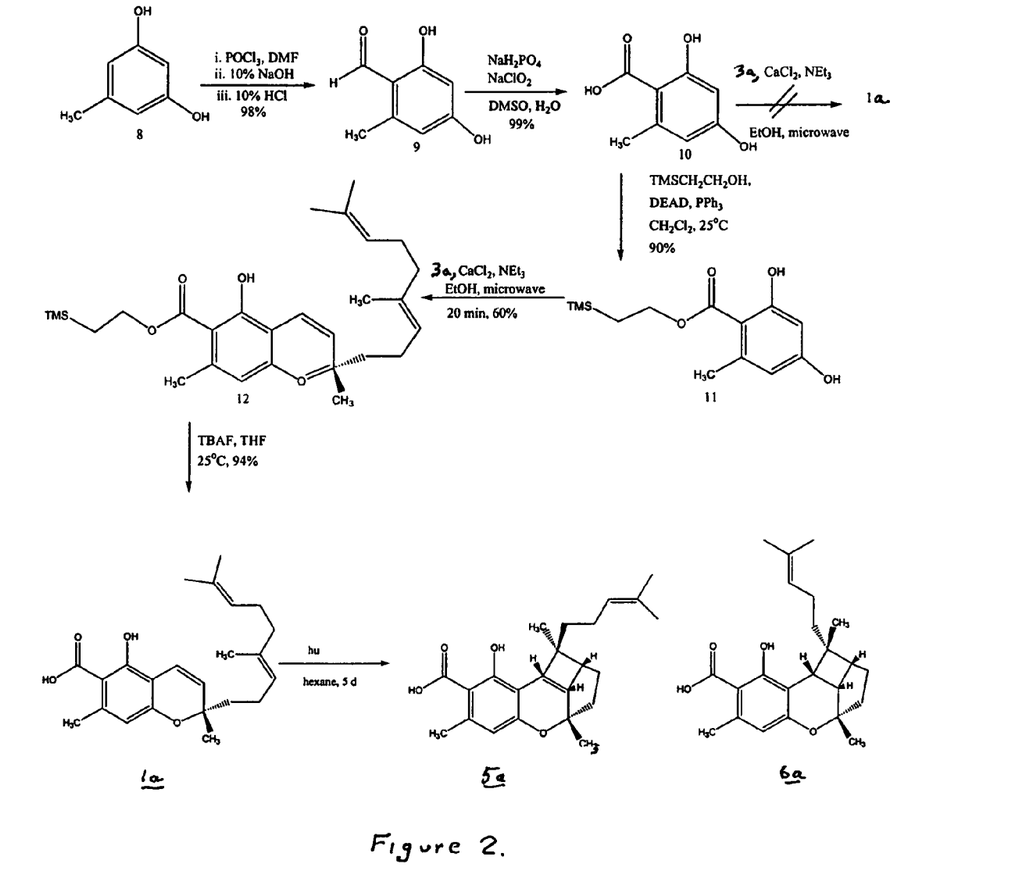

The alternative approach is outlined in FIG. 2. Formylation of orcinol 8 with POCl$_3$ and DMF gave aldehyde 9 (98%), which was oxidized to the corresponding carboxylic acid 10 (NaClO$_2$, 90%). See, Xie, L., et al., *J. Med. Chem.*, 2001, 44, 664 and Nicolaou, K. C. et al., *Chem. Eur. J.*, 2000, 6, 3095. But microwave irradiation of the mixture of compounds 10 and 3a failed to provide any desired product 1a. Therefore, the β-trimethylsilyl ethyl ester 11 was synthesized, that can be easily deprotected to yield the carboxylic acid. Reaction of 10 with 2-(trimethylsilyl)ethanol under Mitsunobu conditions afforded ester 11 in 90% yield (Rousch, W. R., *J. Amer. Chem. Soc.*, 1997, 119, 11331. A mixture of compound 11, aldehyde 3a (2 eq.), $CaCl_2$, $NEt_3$, and EtOH was sealed in a Teflon pressure vessel and was irradiated in the microwave oven for 20 times at 1 minute. The desired product 12 was isolated in 60% yield. Treatment of compound 12 with TBAF gave daurichromenic acid (1a) in 95% yield. Compound 1a was irradiated with a low-pressure mercury lamp for about 5 days to afford a mixture of rhododaurichromanic acids A (40%) (5a) and B (20%) (6a) (based on recovered starting material). The physical data of synthetic daurichromenic acid, and rhododaurichromanic acids A and B are identical to those reported by Kashiwada, Y., *Tetrahedron*, 2001, 53, 1559. The absolute structures of these three compounds were determined based on extensive spectroscopic examination and X-ray crystallographic analysis.

Daurichromenic acid (1a) demonstrates highly potent anti-HIV activity in acutely infected H9 cells with an $EC_{50}$ value of 5.67 ng/mL and therapeutic index (TI) of 3,710. Rhododaurichromanic acids A (2) also shows relatively potent anti-HIV activity with an $EC_{50}$ value of 0.37 mg/mL and a TI of 91.9.

Pharmaceutically acceptable salts of these compounds and their analogs may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as biocidal (anti-bacterial, fungicidal, anti-viral or herbicidal compositions). For example, pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. For example, doses and dosage forms useful to treat mammals infected with HIV or other viral infections are disclosed in U.S. Pat. No. 5,567,703. Dosages for humans and other mammals can be extrapolated from dosages effective in mice by the methods disclosed in U.S. Pat. No. 5,294,430.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In conclusion, the present invention provides a highly efficient total syntheses of daurichromenic acid, rhododaurichromanic acids A and B and analogs thereof. The versatility of microwave technology in the synthesis of 2H-benzo [b]pyrans (chrom-3-enes) has been demonstrated.

All publications and patents are incorporated by reference herein, as though individually incorporated by reference. The invention is not limited to the exact details shown and described, for it should be understood that many variations and modifications may be made while remaining within the spirit and scope of the invention defined by the statements.

What is claimed is:

1. A method for preparing a compound of formula (1)

comprising:
(a) condensing a compound of formula (2):

wherein R' is a carboxylic acid protecting group, with a compound of formula (3):

in the presence of an effective amount of CaCl$_2$, N[(C$_2$–C$_4$)alkyl]$_3$ and [(C$_1$–C$_4$) alkyl]OH and microwave irradiation to yield a compound of formula (4):

(4)

wherein R, X, Y, and Z each independently comprise a moiety selected from hydrogen; C$_1$–C$_{27}$ alkyl optionally straight chain or branched, optionally comprising about 1 to about 4 double bonds; aryl, optionally substituted with about 1 to about 3 alkyl, alkoxy, halo, or N(R$_a$R$_b$) wherein R$_a$ and R$_b$ are independently about C$_1$ to about C$_6$-alkyl; about C$_1$ to about C$_6$-alkoxy; heteroaryl; (about C$_1$ to about C$_{30}$ alkyl)-aryl, wherein the alkyl chain is optionally straight chain or branched and may further comprise about 1 to about 4 double bonds and the aryl group is optionally substituted with about 1 to about 3 alkyl, alkoxy, halo, or N(R$_a$R$_b$) wherein R$_a$ and R$_b$ are independently about C$_1$ to about C$_6$-alkyl; (about C$_1$ to about C$_{30}$ alkyl)-heteroaryl, wherein the alkyl chain is optionally straight chain or branched and may further comprise about 1 to about 4 double bonds; cyano; carboxyamido; alkoxycarbonyl; alkylcarbonyloxy; alkoxycarbonyloxy; or N(R$_a$R$_b$) wherein Ra and Rb are independently H, (about C1 to about C6)-alkyl; and (b) optionally removing protecting R' to yield a compound of formula (1).

2. The method of claim 1 wherein Y is (C$_1$–C$_4$)alkyl.

3. The method of claim 1 wherein Y is methyl.

4. The method of claims 1, 2, or 3 wherein X and/or Z are H.

5. The method of claim 1 wherein N[(C$_2$–C$_4$)alkyl]$_3$ is triethylamine.

6. The method of claim 5 wherein [(C$_1$–C$_4$)alkyl]OH is ethanol.

7. The method of claims 1, 2, 3, or 4 wherein R' is 2-(trimethylsilyl)ethyl.

8. The method of claim 7 wherein R' is removed with tributylammonium fluoride TBAF.

9. The method of claims 1, 2, or 3 wherein R is C$_3$–C$_{22}$ alkyl optionally comprising 1–3 double bonds.

10. The method of claim 9 wherein R is a terpene.

11. The method of claims 1, 2, or 3 wherein X is H, further comprising irradiating the compound of formula 1, wherein R is —CH$_2$CH$_2$CH=C(CH$_3$)R$^2$, wherein R$^2$ is the remainder of organic group R, to yield a compound of formula (6):

(6)

12. The method of claim 11 wherein R$^2$ is —CH$_2$CH$_2$CH=C(Me)$_2$.

13. The method of claim 11 wherein Y is CH$_3$ and Z is H.

* * * * *

UNITED STATES PATENT AND TRADEMARK OFFICE
CERTIFICATE OF CORRECTION

PATENT NO. : 7,102,020 B2
APPLICATION NO. : 10/739882
DATED : September 5, 2006
INVENTOR(S) : Jin et al.

It is certified that error appears in the above-identified patent and that said Letters Patent is hereby corrected as shown below:

In column 3, lines 16-17, delete "rhododurichromenic" and insert
-- rhododaurichromanic --, therefor.

In column 3, line 17, delete "rhododurichromenic" and insert -- rhododaurichromanic --, therefor.

In column 3, line 19, after "(1)" insert -- : --.

In column 3 (Structure 1), lines 23-31, delete "  " and insert
--  --, therefor.

In column 4, line 18, delete "1–2O" and insert -- 1–2 O --, therefor.

In column 4, line 38, delete "Vol. 1" and insert -- Vol. I --, therefor.

In column 10 (Structure 1), lines 32-40, delete "  " and insert
--  --, therefor.

In column 11, line 34, delete "Ra and Rb" and insert -- $R_a$ and $R_b$ --, therefor.

UNITED STATES PATENT AND TRADEMARK OFFICE
CERTIFICATE OF CORRECTION

PATENT NO.         : 7,102,020 B2
APPLICATION NO.    : 10/739882
DATED              : September 5, 2006
INVENTOR(S)        : Jin et al.

It is certified that error appears in the above-identified patent and that said Letters Patent is hereby corrected as shown below:

In column 11, lines 34-35, delete "C1 to about C6" and insert -- $C_1$ to about $C_6$ --, therefor.

Signed and Sealed this

First Day of July, 2008

JON W. DUDAS
*Director of the United States Patent and Trademark Office*